(12) United States Patent
Moriya et al.

(10) Patent No.: US 7,822,261 B2
(45) Date of Patent: Oct. 26, 2010

(54) BOARD INSPECTING APPARATUS, ITS PARAMETER SETTING METHOD AND PARAMETER SETTING APPARATUS

(75) Inventors: Toshihiro Moriya, Nara (JP); Hirotaka Wada, Nara (JP); Takako Onishi, Kyoto (JP); Atsushi Shimizu, Yokohama (JP); Akira Nakajima, Otsu (JP)

(73) Assignee: OMRON Corporation, Kyoto-shi, Kyoto (JP)

( * ) Notice: Subject to any disclaimer, the term of this patent is extended or adjusted under 35 U.S.C. 154(b) by 1162 days.

(21) Appl. No.: 11/472,508

(22) Filed: Jun. 21, 2006

(65) Prior Publication Data

US 2006/0291713 A1    Dec. 28, 2006

(30) Foreign Application Priority Data

Jun. 22, 2005   (JP)  .............................. 2005-182406

(51) Int. Cl.
*G06K 9/00*   (2006.01)
(52) U.S. Cl. ...................................... 382/147
(58) Field of Classification Search ........................ None
See application file for complete search history.

(56) References Cited

U.S. PATENT DOCUMENTS 4,953,100 A    8/1990   Yotsuya et al.
6,023,663 A    2/2000   Kim et al.

FOREIGN PATENT DOCUMENTS

| EP | 1 388 738 A1 | 2/2004 |
|----|--------------|--------|
| JP | 2-78937 | 3/1990 |
| JP | 09 089525 A | 4/1997 |
| JP | 9-145633 | 6/1997 |

OTHER PUBLICATIONS

Patent Abstracts of Japan; Publication No. 02-078937; Date of publication: Mar. 19, 1990 (2 pages).

(Continued)

*Primary Examiner*—Vikkram Bali
*Assistant Examiner*—Elisa M Rice
(74) *Attorney, Agent, or Firm*—Osha • Liang LLP

(57) ABSTRACT

For each teaching image, a plurality of patterns of color pickup regions each include a first region for picking up a color of a first part and a second region for picking up a color of a second part are set, the color of each pixel in the first region and the color of each pixel in the second region are mapped as a target point and an exclusion point respectively, to a color space for each of the patterns of the color pickup regions, a degree in separation between a target point distribution and an exclusion point distribution in the color space is calculated for each of the patterns of the color pickup regions, a pattern of a color pickup region having a maximum degree in separation is selected, a color range which divides the color space and has the largest difference between the number of target points and the number of exclusion points in the selected pattern therein is found, and the found color range is set as a color condition used in a board inspecting process.

9 Claims, 14 Drawing Sheets

OTHER PUBLICATIONS

Patent Abstracts of Japan; Publication No. 09-145633; Date of Publication: Jun. 6, 1997 (2 pages).

European Search report dated Oct. 12, 2007, issued in European Application No. 06115773.Jan. 2204, 7 pages.

Capson D W et al., "A Tiered-Color Illumination Approach for Machine Inspection of Solder Joints" IEEE Transactions on Pattern Analysis and Machine Intelligene, vol. 10, No. 3, May 1988, 7 pages.

Patent Abstracts of Japan, Publication No. 09089525 dated Apr. 4, 1997, 1 page.

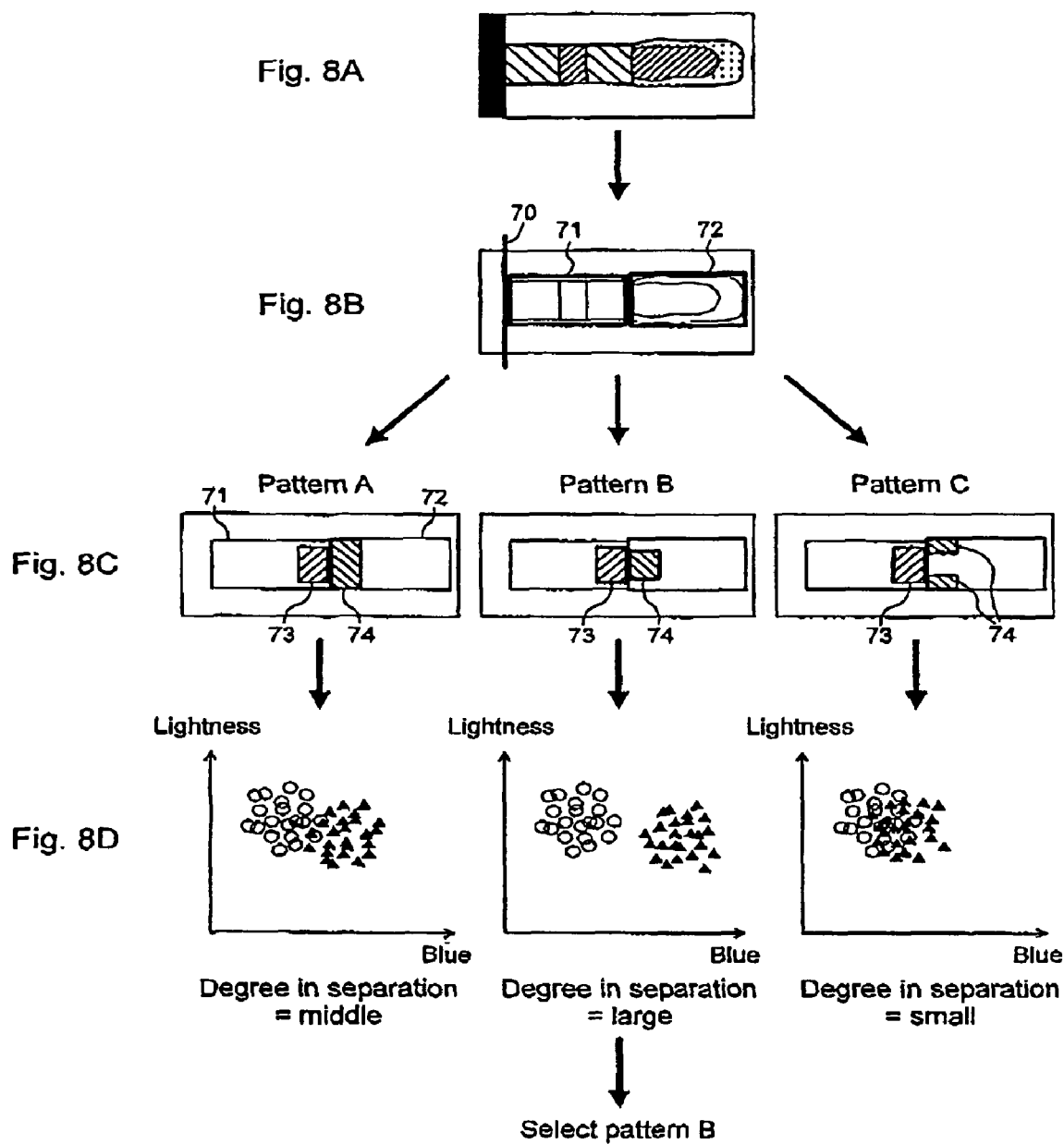

PRIOR ART

PRIOR ART

PRIOR ART

BOARD INSPECTING APPARATUS, ITS PARAMETER SETTING METHOD AND PARAMETER SETTING APPARATUS

BACKGROUND OF THE RELATED ART

1. Field of the Invention

The present invention relates to a technique for automatically generating a parameter used for a board inspecting apparatus.

2. Description of the Background Art

Conventionally, board inspecting apparatuses for inspecting a mounted quality on a PC board on which a number of electronic components are mounted have been proposed. According to the PC board, although a "configuration of soldered part between an electrode of an electronic component and a land" is called a solder fillet, there is a case the solder fillet seems to be formed but the electronic component is not in contact with the solder fillet actually depending on a rise at the electrode of the electronic component. Thus, when it is inspected whether soldering is good or not, it is necessary to grasp a configuration of the solder fillet comprising a free curved line correctly.

However, according to the conventional board inspecting apparatus, since a monochrome (single-color) light source is used, it is difficult to analyze an image of a three-dimensional configuration of the solder fillet. Therefore, determination whether the soldering is good or not cannot be made, so that the board inspecting apparatus cannot be put into practical use.

A method for solving the above mentioned problem is presented as a board inspecting apparatus of a system, shown in FIG. 11 (see Japanese Unexamined Patent Publication No. 2-78937). This system is called a three-color light source color highlight system (or simply called a color highlight system), in which a three-dimensional configuration of the solder fillet can be provided as a pseudo-color image by irradiating an inspection target with light sources having a plurality of colors.

As shown in FIG. 11, the board inspecting apparatus of the color highlight system comprises a light emitter 105 that irradiates an inspection target 107 on a board 110 with three primary colors of rays at different angles of incidence, and an imaging device 106 that captures an image formed by reflection light of the color rays from the inspection target 107.

When the inspection target (solder fillet) 107 is irradiated with the light emitter 105 having the above constitution, a color light corresponding to the inclination of the surface of the inspection target 107 is inputted to the imaging device 106. Thus, as shown in FIG. 12, color patterns of the captured images are clearly different depending on the configurations of the solder fillets in cases where the soldering of the electronic component is good and where the component is missing and where the solder is insufficient. Thus, since the image of the three-dimensional configuration of the solder fillet can be easily analyzed, determination whether the electronic component is missing or not, or whether the soldering is good or not can be correctly made.

According to the board inspecting apparatus of the color highlight system, a color parameter (color condition) showing a "color to be detected in an acceptable part" or a "color to be detected in a defective part" is previously set and a color region corresponding to the color parameter is extracted from an inspection image and determination is made on the basis of various kinds of features (an area value and a length, for example) in the extracted region. Therefore, it is necessary to previously set the color parameter, the kind of the feature, a determination condition (a threshold value, for example) to separate a good part and a defective part, which are used in an inspecting process, prior to the substantial inspecting process. The color parameter, the feature and the determination condition are called inspection logic or an inspection parameter; in general to set or adjust the inspection logic is called teaching.

In order to improve inspection precision, it is important to set the color parameter so that a significant and a clear difference may be generated between the feature of the good part and the feature of the defective part. That is, the inspection precision is directly affected by a quality of the teaching of the color parameter.

Thus, as shown in FIG. 13, the applicant of the present invention proposes a tool to support the setting of the color parameter in the color highlight system (see Japanese Unexamined Patent Publication No. 9-145633). According to the tool, an upper limit value and a lower limit value of each of the hue ratios ROP, GOP and BOP of red, green and blue, respectively and lightness data BRT can be set as the color parameters. Thus providing means for so the operator can search for the color parameter to obtain an appropriate extracted result while seeing the confirmation region 135 or the binary image.

The board inspecting apparatus has an advantage such that a plurality of inspection items regarding the mounted quality of the PC board can be inspected at one time at high speed with high precision. However, when the board inspecting apparatus is actually operated, it is necessary to perform a teaching operation for each inspection logic according to each inspection target to sufficiently enhance determination precision so as not to miss a defective part and so as to suppress over-detection which determines a good part as a defective part, below an allowable value (previously assumed value).

According to the board inspecting apparatus of the color highlight system, while the board inspecting apparatus can be implemented with high precision for practical use, the teaching operation to prevent the defective part from being missed and to suppress the over-detection below a target value is difficult.

Even when the above color parameter setting support tool is used, since the color parameter is searched relies on the experience and intuition of the operator, a setting miss cannot be avoided. Furthermore, since even a superior operator needs to repeat adjustment through trial and error, this is not efficient and needs a large amount of labor and a long adjustment time.

In frequently changing manufacturing circumstances in which a product life cycle is shortened, it is highly desired that the teaching operation is simplified and furthermore the teaching is automatically performed.

In addition, there is a case where a position of a part to be inspected (solder part or land part or the like) varies according to each component (each captured image) depending on a component kind, and when such component kind is inspected, a process to specify an inspection target region from the image with high precision is needed. For example, in a case of a component having the Gullwing type of lead, a length of the lead (on the image) varies in many cases. Therefore, in order to inspect a solder fillet configuration etc., formed on a land, it is necessary to find a boundary between a lead part first and a solder part and extract only the solder part from the image.

Since an edge part of the lead is horizontal, a red color (of a light source having largest incident angle) tends to appear at the edge part of the lead in the board inspecting apparatus of the color highlight system.

Meanwhile, since the solder part close to the edge of the read is inclined, a blue or green color (of a light source having a small incident angle) tends to appear there. Therefore, when a difference in color distribution tendency is detected, the boundary between the lead and the solder can be determined. That is, by teaching the color of the lead part and the color of the solder part and then matching the colors with their color conditions, the boundary can be specified.

However, the reality is not that simple because a color tendency appearing at the solder part varies depending on the component kind.

For example, the configuration (inclination) of the solder fillet is not uniform and a horizontal surface could be formed in the vicinity of the edge of the lead. Regarding a component having many leads like an IC component especially, since a lead width and an interval of the leads is small, a width of a solder is also small, and it is highly likely that a horizontal surface is formed in the solder fillet. As FIG. 14 shows images of three kinds of components, according to a component kind A, a color of blue kind appears at an entire boundary between the lead and the solder, according to a component kind B, the color of blue kind appears only at the center of a boundary, and according to a component kind C, the color of blue kind appears only at both ends of a boundary.

Such variation in color distribution tendency hinders the teaching from being automatically performed. In addition, the same problem arises in not only the process for specifying the boundary between the lead part and the solder part but also in almost all process for specifying the boundary between adjacent two parts.

SUMMARY

Several embodiments of the present invention provide a technique for automatically generating a parameter used for specifying a boundary between adjacent two parts in an image.

Furthermore, tone or more embodiments of the invention provide a technique for automatically generating the parameter even from a teaching image having a variation in color distribution tendency.

In an embodiment of the present invention, an information processor (parameter setting apparatus) obtains a plurality of teaching images provided from images of components, and sets a plurality of patterns of color pickup regions each comprising a first region for picking up a color of a first part and a second region for picking up a color of a second part for each teaching image.

Each of the first region and the second region has a predetermined configuration and size. The entire first part may be the first region or a part of the first part may be set to the first region. The same is true of the second region. The configuration and size of each pattern is preferably determined according to a tendency of the color distribution of the teaching image. For example, when it is known that there are three kinds of cases such as a case where a characteristic color of the second part appears at the entire part of the second part, a case where it appears only at the center of the second part, or a case where it appears only an end of the second part, only three kinds of patterns such as a pattern that covers the entire part of the second part, a pattern that covers only the center thereof and a pattern that covers only the end thereof have to be prepared.

Then, the information processor maps a color of each pixel in the first region as a target point and a color of each pixel in the second region as an exclusion point in each pattern of the color pickup region to a color space. Then, it calculates a degree in separation between a target point distribution and an exclusion point distribution for each pattern of the color pickup region and selects a pattern of a color pickup region having the maximum degree in separation.

Thus, the pattern of the color pickup region having the largest difference in color distribution tendency between the first and second regions is determined.

Then, the information processor finds a color range which divides the color space and having the maximum difference between the number of the target points and the number of the exclusion points in the selected pattern, and sets the found color range to a color condition used for the board inspecting process.

Thus, the color condition which is one of the parameters is automatically generated. In addition, since the color condition is generated using the pattern of the color pickup region having the largest difference in color distribution tendency, the color having a tendency to appear in the first part and the color having a tendency to appear in the second part can be appropriately cut.

Here, although the color space may be a multidimensional color space comprising at least three axes of lightness, hue and chroma, it may be preferable that a two-dimensional color space comprising a chroma axis and a lightness axis for a hue having a tendency to be included much in the first part but hardly included in the second part, or a hue having a tendency to be included much in the second part but hardly included in the first part is used. When the two-dimensional color space is used, a searching process of the color range becomes simple. In addition, when the color condition consists of lower and upper limit values of chroma and lower and upper limit values of lightness in the two-dimensional space, its color range is a rectangular region, so that the searching process of the color range becomes more simple.

Then, the information processor extracts a pixel region which satisfies the color condition from each teaching image and statically analyzes a feature in the pixel region to calculate a condition for determining a boundary between the first part and the second part and sets the calculated condition as a determination condition used for the board inspecting process. Thus, the determination condition which is one of the parameters is automatically generated.

The features here include an area value, an area ratio, a length, a maximum width, a centroid, a configuration of the pixel region and a combination of those. One or more features may be employed depending on the target to be inspected.

The above each process is executed by a program of the information processor. The automatically generated parameters (the color condition and the determination condition) are stored in a storage of a board inspecting apparatus and used for the board inspecting process.

A board inspecting apparatus comprises a light emitter for irradiating a mounted component on a board with a plurality of color rays at different incident angles; a boundary determining device for determining a boundary between a first part and a second part adjacent to the first part on the board in an image of their reflected light by extracting a region that satisfies a predetermined color condition which defines a color having a tendency to appear in the first part, from the image and comparing a feature in the extracted region with a predetermined determination condition to specify the boundary; and an inspecting device for extracting an inspection target region on the basis of the boundary and inspecting the inspection target region. When the color condition and the determination condition generated by the above parameter setting apparatus are used, the boundary between the first and second parts can be specified with high precision, so that the inspection target region can be appropriately set and precision and reliability of the board inspecting process can be improved.

In addition, several of the embodiments of the present invention can be applied as a parameter setting method of a board inspecting apparatus comprising at least one part of the above process, or a program for implementing that method. Furthermore, several of the embodiments of the present invention can be implemented as a parameter setting apparatus of a board inspecting apparatus having at least one part of the above device, or a board inspecting apparatus comprising the above apparatus. The above device and process can be combined as much as possible to constitute and still remain within the scope of the present invention.

According to an embodiment of the present invention, the parameter used for specifying the boundary between the two adjacent parts can be automatically generated even from the teaching image having a variation in color distribution tendency, so that the teaching operation can be simplified and the teaching can be automatically provided.

BRIEF DESCRIPTION OF THE DRAWINGS

FIG. 8 shows a color pickup region determining process;

DETAILED DESCRIPTION

One exemplary embodiment of the present invention will be described in detail with reference to the drawings hereinafter.

(Constitution of Board Inspecting System)

Figure 1:
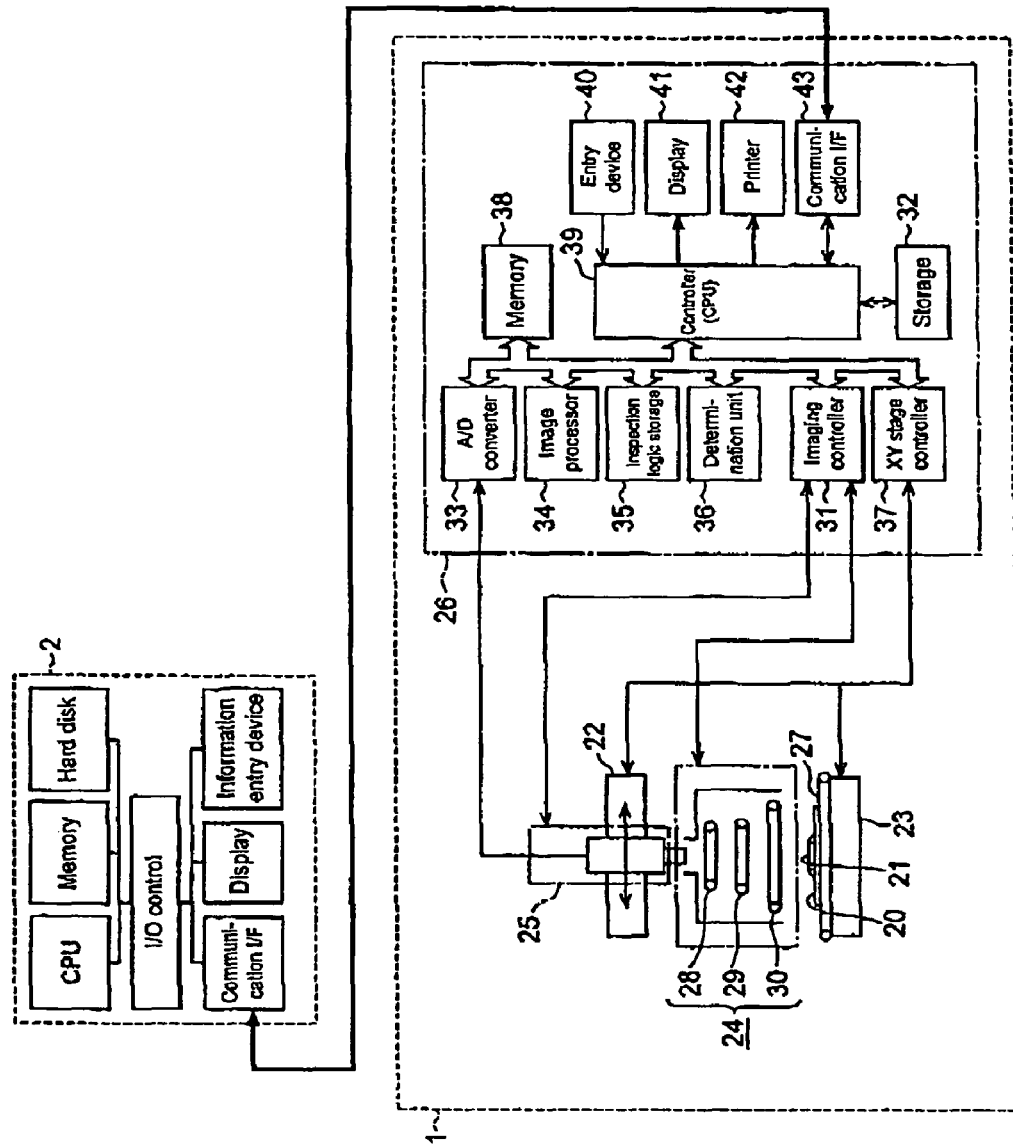
FIG. 1 shows a hardware constitution of a board inspecting system according to an embodiment of the present invention.

FIG. 1 shows a hardware constitution of a board inspecting system according to one embodiment of the present invention.

The board inspecting system comprises a board inspecting apparatus 1 that executes a board inspecting process, and a parameter setting apparatus 2 that automatically generates parameters for use in the board inspecting process of the board inspecting apparatus 1. The board inspecting apparatus 1 and the parameter setting apparatus 2 can receive and transmit electronic data such as an image or a parameter through a wired or wireless network or a recording medium such as an MO or DVD. In addition, although the board inspecting apparatus 1 and the parameter setting apparatus 2 are separately provided in this embodiment, they can be integrated by incorporating the function of the parameter setting apparatus in a body of a board inspecting apparatus.

(Constitution of Board Inspecting Apparatus)

The board inspecting apparatus 1 automatically inspects a mounting quality (such as a soldering state) of a mounted component 21 on a board 20 by a color highlight system. The board inspecting apparatus 1 comprises, roughly, an X stage 22, a Y stage 23, a light emitter 24, an imaging device 25, and a control processor 26.

Each of the X stage 22 and the Y stage 23 has a motor (not shown) which operates on the basis of a control signal from the control processor 26. By the driving of the motors, the X stage 22 moves the light emitter 24 and the imaging device 25 in the X axis direction, and the Y stage 23 moves a conveyer 27 supporting the board 20 in the Y axis direction.

The light emitter 24 is constructed by three annular light sources 28, 29 and 30 having different diameters and simultaneously emitting red light, green light and blue light on the basis of the control signals from the control processor 26. The light sources 28, 29 and 30 are disposed so that their centers are adjusted to a position directly above an observation position, in directions corresponding to their angles of elevation which are different from each other when seen from the observation point. By the arrangement, such light emitter 24 emits a plurality of color rays (of the three colors of R, G and B in the embodiment) which are incident on the mounted component 21 on the board 20 at different angles of incidence.

The imaging device 25 is a color camera and is positioned so as to face downward in the position directly above the observation position. Reflection light from the board surface is captured by the imaging device 25 and is converted to the color signals R, G and B of the three primary colors. The color signals R, G and B are supplied to the control processor 26.

The control processor 26 includes an A/D converter 33, an image processor 34, an inspection logic storage 35, a determination unit 36, an imaging controller 31, an XY stage controller 37, a memory 38, a controller (CPU) 39, a storage 32, an entry device 40, a display 41, a printer 42, and a communication I/F 43.

The A/D converter 33 is a circuit for receiving the color signals R, G and B from the imaging device 25 and converting them to digital signals. Gradation image data of a digital amount of each hue is transferred to an image data storing area in the memory 38.

The imaging controller 31 is a circuit including an interface connecting the controller 39 and the light emitter 24 and the imaging device 25. The imaging controller 31 adjusts the light amount of each of the light sources 28, 29 and 30 of the light emitter 24 on the basis of an output of the controller 39 and controls mutual balance among light outputs of different hues of the imaging device 25 to maintain it.

The XY stage controller 37 is a circuit including an interface connecting the controller 39 and the X and Y stages 22 and 23, and controls driving of the X and Y stages 22 and 23 on the basis of an output of the controller 39.

The inspection logic storage 35 is a storage for storing an inspection logic used for the board inspecting process. The board inspecting apparatus 1 can perform a plurality of kinds of inspecting processes such as a fillet inspection for inspecting the configuration of a solder and a completeness inspection for inspecting a missing component. The inspection logic is prepared for each kind of inspections and comprises a color parameter for extracting a predetermined color pattern from an image, a kind of a feature extracted from the color pattern and a determination condition for determining a quality regarding the feature.

In addition, among the inspection logics, a process for specifying an inspection target region to be inspected (inspection target region determining process) is performed prior to the inspecting process in some cases. Such inspection logic includes a parameter for the inspection target region determining process in addition to the parameter (the color parameter, the kind of the feature and the determining condition) for the inspecting process. The parameter for the inspection target region determining process includes a color parameter (color condition) for extracting a predetermined color pattern (pixel region) from the image, a kind of the feature extracted from the color pattern and a determination condition for determining a boundary in the region based on the feature.

The image processor 34 is a circuit for executing a process of extracting a region which satisfies the color parameter from the captured image of the component 21 on the board 20 and a process of calculating the predetermined feature from the extracted region. The determination unit 36 is a circuit that receives the feature calculated by the image processor 34 and executes a process of determining whether the component is mounted in a good state or not on the basis of whether the feature satisfies the predetermined determination condition or not or executes a process of determining the boundary in the inspection target region.

The entry device 40 includes a keyboard and a mouse necessary to enter operation information, data on the board 20, and the like. The entered data is supplied to the controller 39. The communication I/F 43 is used to transmit or receive data among the parameter setting apparatus 2 and other external devices.

The controller (CPU) 39 is a circuit for executing various computing processes and control processes. The storage 32 is a memory device comprising a hard disk, a memory, or the like and stores not only programs executed in the controller 39 but also CAD data of the board, results of determination of the board inspecting process, and the like.

Figure 2:
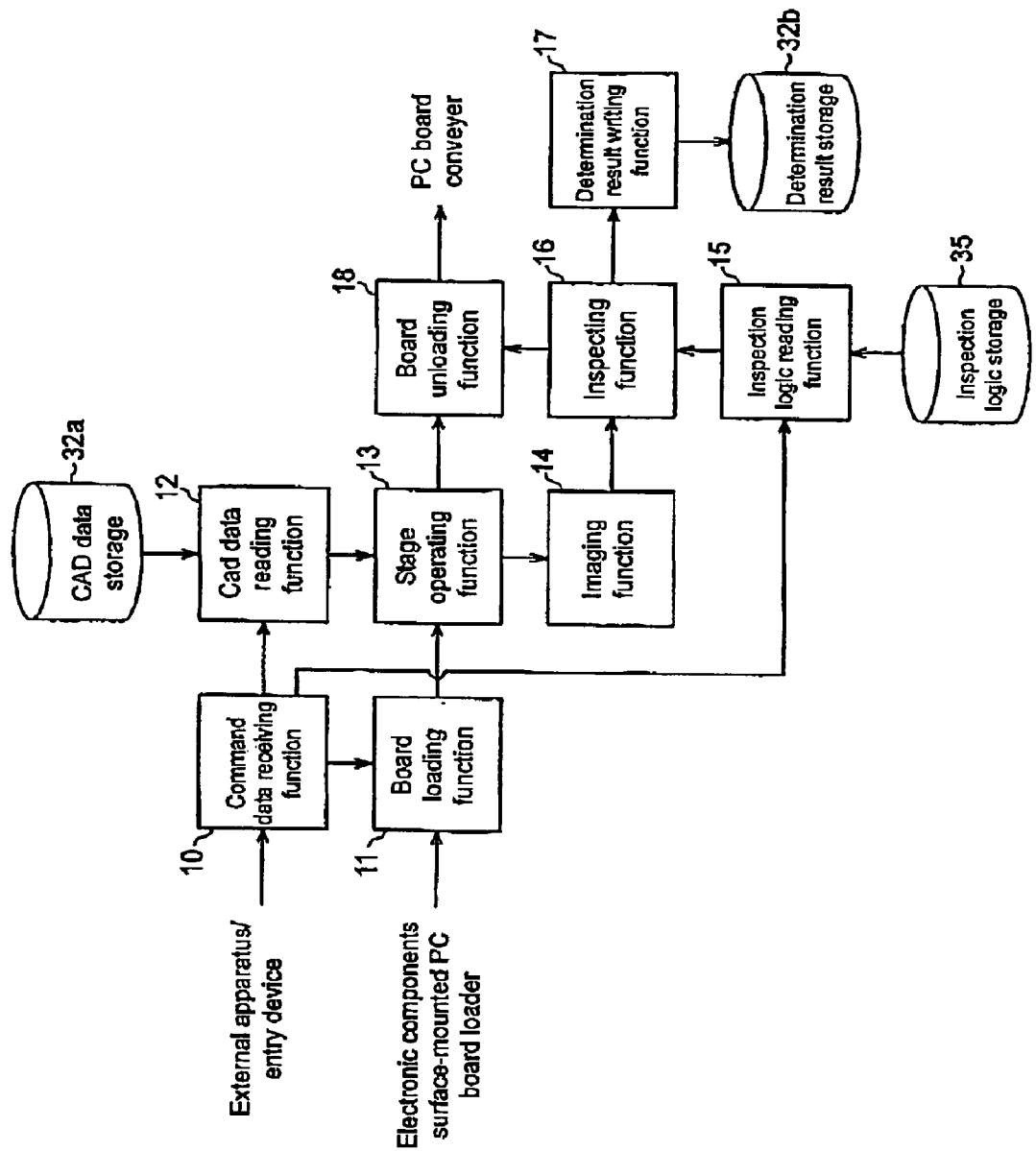
FIG. 2 shows a functional constitution of a board inspecting apparatus.

FIG. 2 shows a functional constitution of the board inspecting apparatus 1. The board inspecting apparatus 1 has a command data receiving function 10, a board loading function 11, a CAD data reading function 12, a stage operating function 13, an imaging function 14, an inspection logic reading function 15, an inspecting function 16, a determination result writing function 17, and a board unloading function 18. Those functions are realized when the controller 39 controls the hardware in accordance with a program stored in the storage 32. The storage 32 has therein a CAD data storage 32a for storing CAD data and a determination result storage 32b for storing a determination result.

(Board Inspecting Process)

Next, the board inspecting process in the board inspecting apparatus 1 will be described. As one example of the board inspecting process, a fillet inspection (an inspection to determine whether the configuration of the solder fillet is good or not) will be described.

Figure 3A:
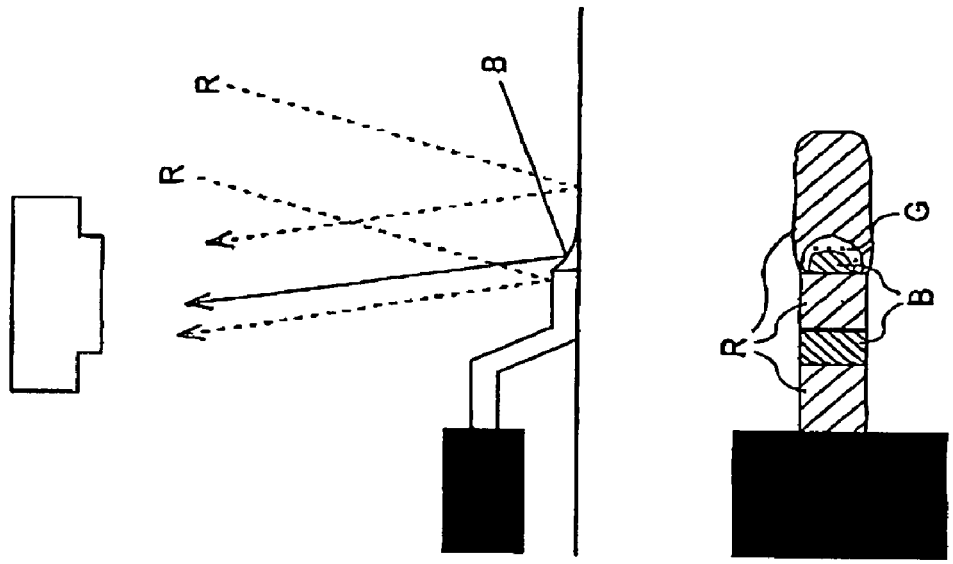
FIG. 3 shows a relation between a configuration of a solder fillet and a captured image pattern.

As shown in FIG. 3A, a gentle slope like a foot of a mountain is formed from a lead edge of the component 21 toward a land on the board 20 in a good solder fillet. Meanwhile, when the solder is not sufficient, the slope becomes steep.

Figure 3B:
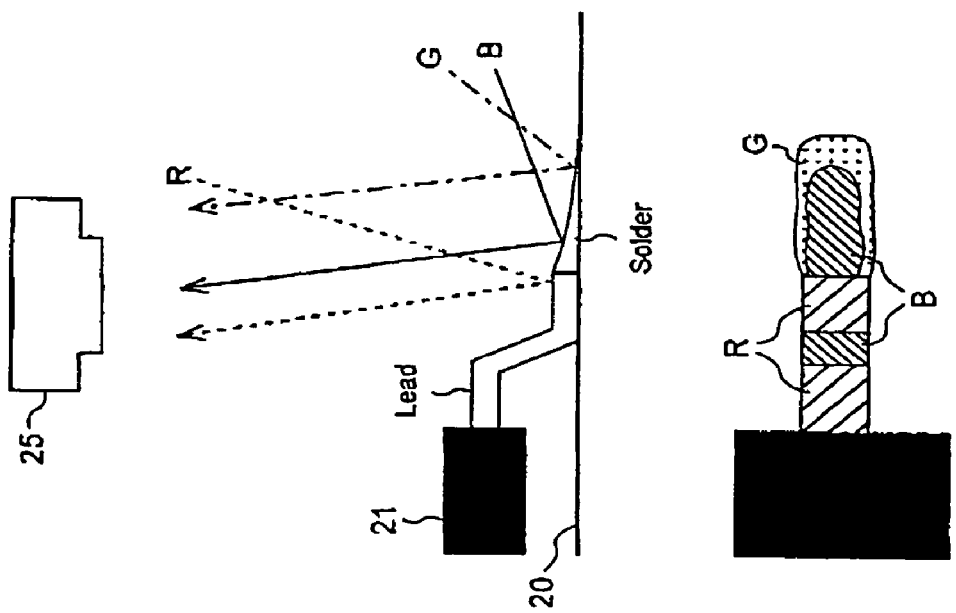

When the images of those solder fillets are taken by the board inspecting apparatus 1, they are provided as shown in FIG. 3B. Since the red, green and blue rays enter the solder fillet at different angles, the hue of the reflected light that enters the imaging device 25 varies depending on the slope of the solder fillet. That is, while the reflected light of the blue ray having the smallest incident angle is dominant at a steep slope, the reflected light of the red ray is dominant at the gentle slope. Therefore, while a region of the blue hue is largely provided in the good solder fillet, a region of a hue other than blue is largely provided in the defective solder fillet. According to the fillet inspection in this embodiment, such tendency of the color pattern is used to determine whether the solder fillet is good or not on the basis of the size (area value) of the blue color region.

Meanwhile, not only the solder part which is to be inspected but also the lead (electrode) of the component is shown in the image. Since the edge of the lead (adjacent to the solder) is horizontal with respect to the board, this part shows the red color in the image. That is, since the color of the lead part is likely to be confused with the color of the defective solder part, precision of the fillet inspection could be lowered.

Figure 4:
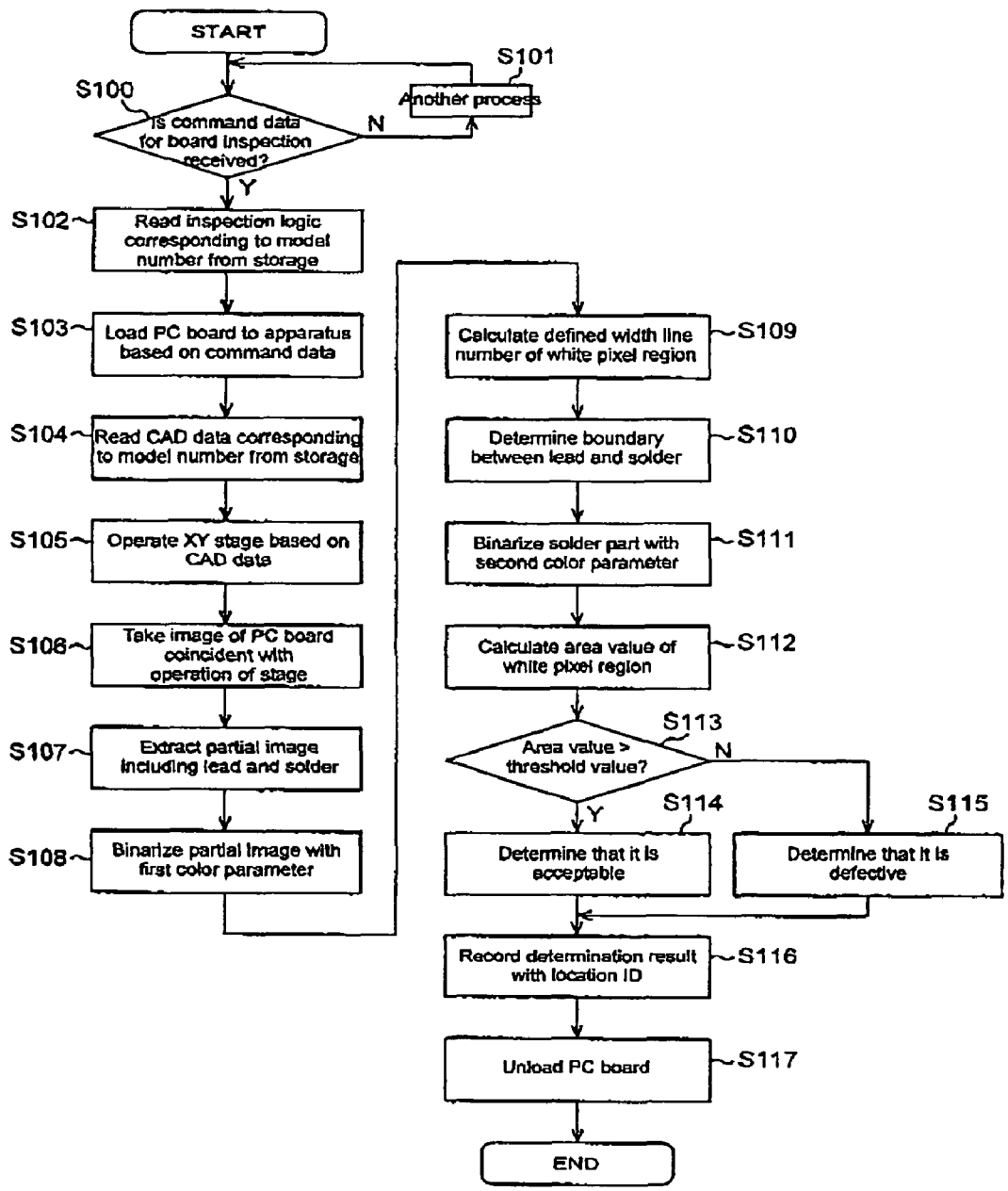
FIG. 4 shows a flowchart showing a flow of a board inspecting process.

Thus, according to this embodiment, the inspection target region determining process for determining the boundary between the lead part and the solder part and extracting only the solder part to be inspected is performed prior to the inspecting process. The process of imaging the mounted component on the board, the process of determining the inspection target region, and the inspecting process will be described in turn according to a flowchart shown in FIG. 4 hereinafter.

(1) Component Imaging Process

The command data receiving function 10 is in a standby state until command data that instructs execution of a board inspection is entered (NO at step S100) (at step S101). When the command data is entered by the operation of the entry device 40 or from an external device via the communication I/F 43, the command data receiving function 10 sends the command data to the board loading function 11, the CAD data reading function 12, and the inspection logic reading function 15 (YES at step S100). The command data includes information (such as a model number) of a board to be inspected.

The inspection logic reading function 15 reads an inspection logic corresponding to the model number of the board from the inspection logic storage 35 (at step S102). Here, the inspection logic for inspecting the fillet is read out. This inspection logic includes a first parameter set for the inspection target region determining process and a second parameter set for the inspecting process. The first parameter set includes a first color parameter for a binarizing process and a first determination condition for determining the boundary. The second parameter set includes a second color parameter for a binarizing process and a second determination condition for determining whether the part is good or not.

The board loading function 11 loads the board 20 to be inspected from a PC board loading part onto the conveyer 27 on the basis of the command data (at step S103). The CAD data reading function 12 reads CAD data corresponding to the model number of the board from the CAD data storage 32a (at step S104).

Next, the stage operating function 13 obtains data such as the dimensions and configuration of the board 20 and the layout of the components from the read CAD data and operates the X stage 22 and the Y stage 23 via the XY stage controller 37 so that a plurality of components 21 mounted on the board 20 are positioned sequentially in an observation position (image pickup position) (at step S105).

On the other hand, the imaging function 14 makes the three light sources 28, 29 and 30 of the light emitter 24 emit lights via the imaging controller 31 to simultaneously irradiate the board 20 with lights of red, green and blue. The imaging function 14 controls the imaging device 25 via the imaging controller 31 and captures an image of the component 21 on the board 20 synchronously with the operations of the stages 22 and 23 (at step S106). The captured image is stored in the memory 38.

(2) Inspection Target Region Determining Process

Figure 5A:
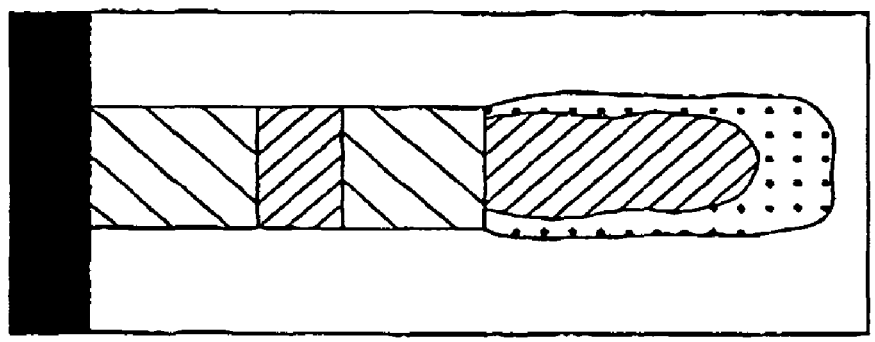
FIG. 5 shows an inspection target region determining process.
Figure 5B:
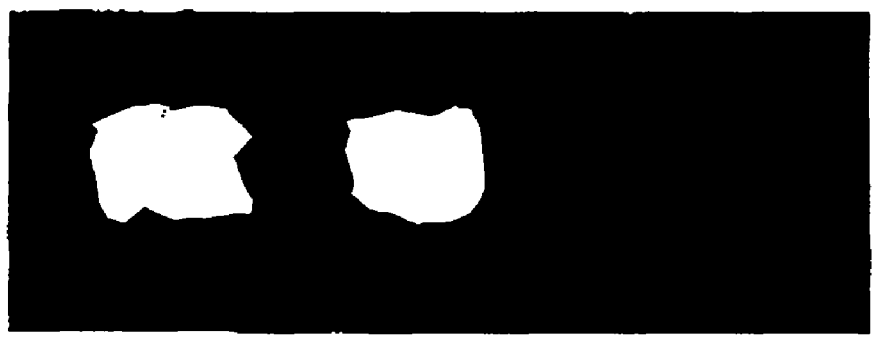

As shown in FIG. 5A, the inspecting function 16 extracts a partial image including the lead and the solder from the captured image by the image processor 34 (at step S107). Then, the inspecting function 16 converts the extracted partial image into a binary form by using the first color parameter (at step S108). The first color parameter is a color condition to define the color (red color) that tends to appear at the lead part, and comprises four values of upper and lower limit values of chroma and upper and lower limit values of lightness of the red color. According to the process for converting the image into the binary form, pixels contained in a color range defined by the color parameter are converted to white pixels and pixels other than the above pixels are converted to black pixels. Thus, in the image after converted to the binary form, a large white pixel region appears in the lead part as shown in FIG. 5B.

Figure 5C:
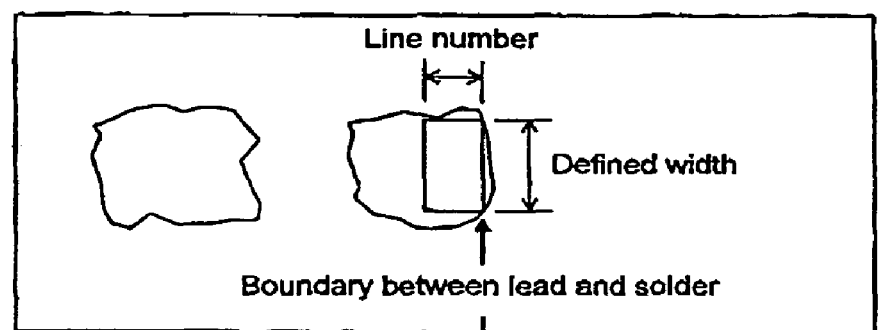

Subsequently, the inspecting function 16 extracts a feature of the white pixel region by the image processor 34 (at step S109). More specifically, as shown in FIG. 5C, the inspecting function 16 extracts a line having a width defined by the first determination condition (referred to as the "defined width" hereinafter) or more (referred to as the "defined width line" hereinafter) among lines constituting the white pixel region, and calculates the number of the defined width lines (pixels) which are aligned in succession (referred to as the "defined width line number).

Then, the inspecting function 16 compares the defined width line number with a threshold value contained in the first determination condition to determine the boundary between the lead part and the solder part (at step S110). For example, when the threshold value is set to five, the inspecting function 16 regards a range in which the number of the defined width lines which are sequentially aligned in the white pixel region is five or more (5 pixels) as the lead part and regards an edge of the lead part as the boundary between the lead and the solder.

Thus, the boundary between the lead part and the solder part can be automatically determined and only the image of the solder part to be inspected (inspection target region) can be extracted.

(3) Inspecting Process

Figure 5D:

The inspecting function 16 converts the image of the solder part extracted by the inspection target region determining process into a binary form by using the second color parameter (at step S111). The second color parameter is a color condition to define the color (blue kind color) which tends to appear in the good solder part and comprises four values of upper and lower limit values of chroma and upper and lower limit values of lightness of the blue color. When the image is converted to the binary form by the second color parameter, the blue kind color part of the solder can be extracted as the white pixel region as shown in FIG. 5D.

Then, the inspecting function 16 calculates an area value of the white pixel region as a feature of the white pixel region (at step S112). Thus, the area value is sent to the determination unit 36 and the determination unit 36 compares the area value of the white pixel region with a threshold value of the second determination condition (at step S113). When the area value exceeds to the threshold value, it is determined that the solder mounted quality of that part is good (at step S114) and when the area value is not more than the threshold value, it is determined that the quality is defective (at step S115).

The determination result writing function 17 writes the determination result together with a location ID (data for specifying the component) into the determination result storage 32b (at step S116).

After completion of inspections on all of the components on the board 20, the board unloading function 18 unloads the board 20 by a PC board conveyer, and the board inspecting process is finished (at step S117).

According to the board inspecting process described above, since the three-dimensional configuration of the solder fillet can be clearly grasped by the color pattern appearing in the two-dimensional image, it can be determined whether the solder mounted quality is good or not. In addition, since the color of the lead part which could become a noise at the time of determination can be automatically removed, determination precision is improved.

Meanwhile, in order to implement high determination precision in which a defective component is surely found and over-detection is not more that an allowable value, it is necessary to set a parameter of the inspection logic to an optimum value according to the inspection target previously. According to this embodiment, generation (teaching) of these parameters is automatically performed by the parameter setting apparatus 2. Hereinafter, a process for generating the first color parameter and the first determination condition for the inspection target region determining process will be described in detail.

(Constitution of Parameter Setting Apparatus)

As shown in FIG. 1, the parameter setting apparatus 2 is a general-purpose computer (information processor) comprising, as basic hardware, a CPU, a memory, a hard disk, an I/O control unit, a communication I/F, a display, information entry devices (keyboard and mouse).

Figure 6:
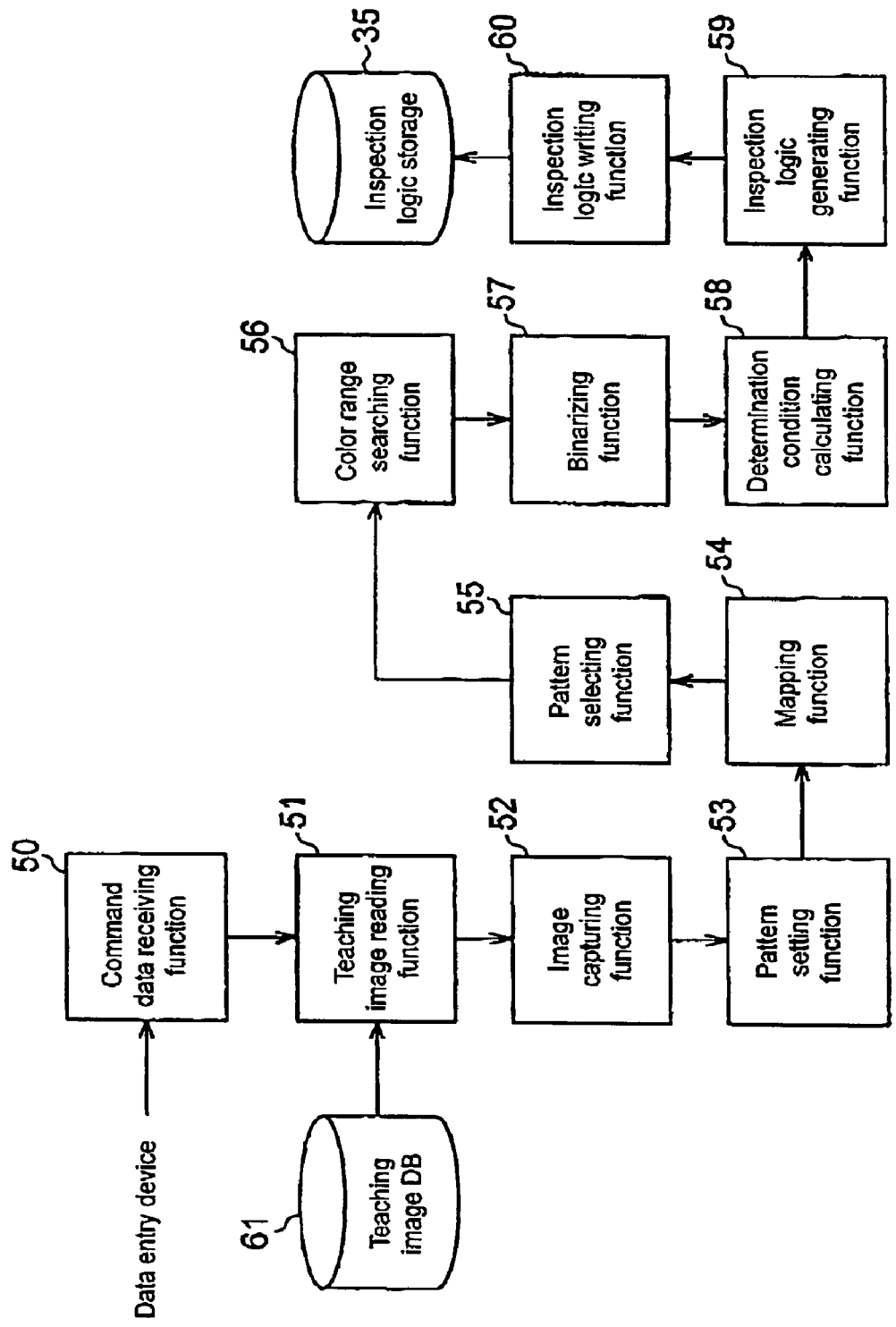
FIG. 6 shows a functional constitution of a parameter setting apparatus.

FIG. 6 shows a functional constitution of the parameter setting apparatus 2. The parameter setting apparatus 2 comprises a command data receiving function 50, a teaching image reading function 51, an image capturing function 52, a pattern setting function 53, a mapping function 54, a pattern selecting function 55, a color range searching function 56, a binarizing function 57, a determination condition calculating function 58, an inspection logic generating function 59, and an inspection logic writing function 60. The functions are realized when a program stored in the memory or the hard disk is loaded to the CPU and executed.

In the hard disk, a teaching image DB 61 for storing a teaching image used for teaching is provided. The teaching image is an image of a mounted component taken by the board inspecting apparatus 1. When the parameter for the inspection target region determining process is generated, it is preferable that only the image of a good sample is used as the teaching image because a good part has a clearer difference in color distribution tendency between the lead and solder. In addition, in order to enhance the reliability of the teaching, it is preferable to prepare tens to thousand of pieces of teaching images.

(Parameter Setting Process)

Figure 7:
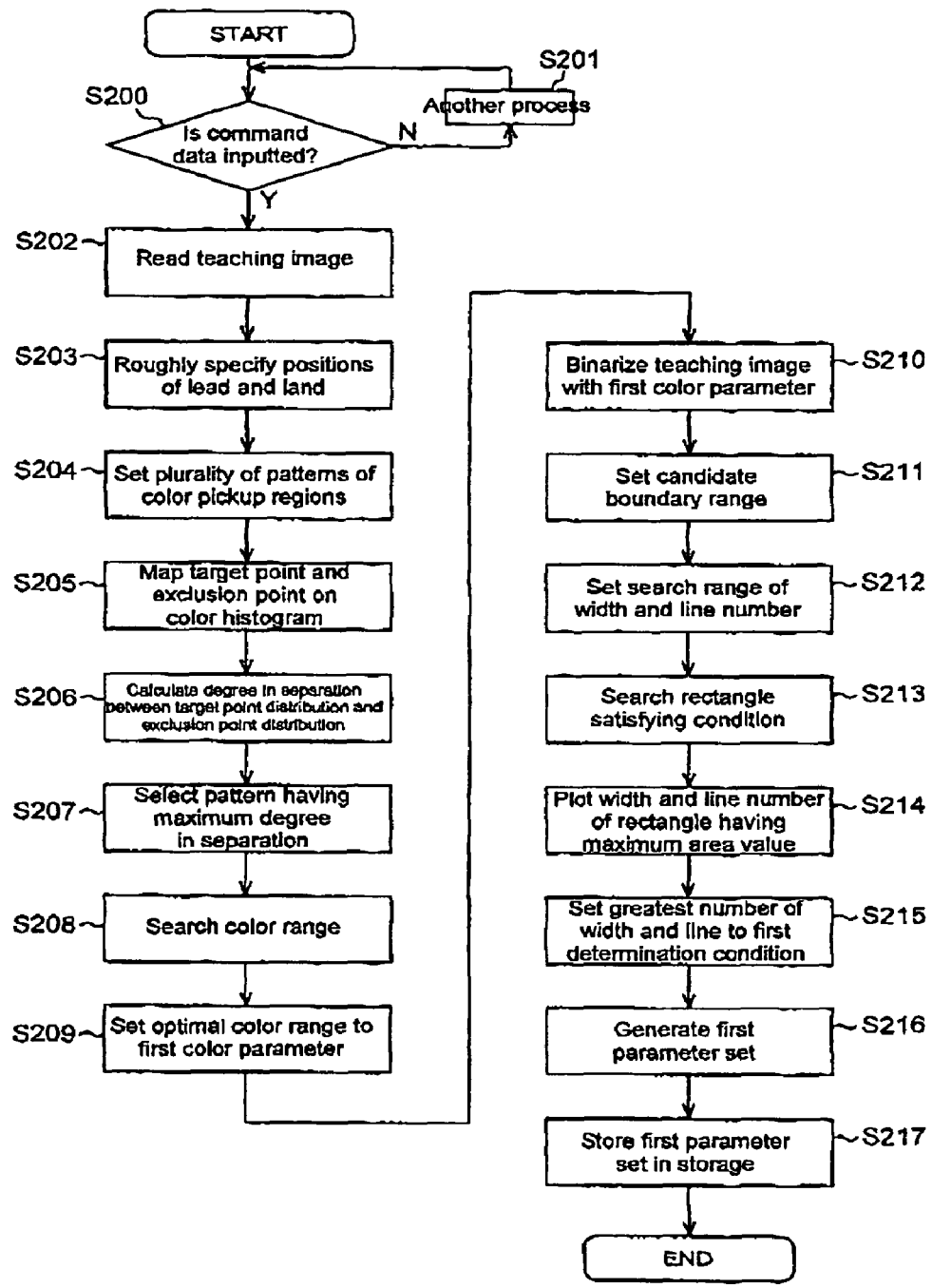
FIG. 7 shows a flowchart showing a flow of a parameter setting process for the inspection target region determining process.

The flow of the parameter setting process will be described with a flowchart shown in FIG. 7.

The command data receiving function 50 is in a standby state until command data that instructs automatic generation of the inspection logic is entered (NO at step S200) (at step S201). When the command data is entered from the command entry device, the command data receiving function 50 transmits the command data to the teaching image reading function 51 (YES at step S200). This command data includes data that specifies a teaching image as an object of generation of the inspection logic, data of a kind of inspection logic and the like.

The teaching image reading function 51 reads a plurality of teaching images corresponding to the inspection logic to be generated from the teaching image DB 61 according to the command data (at step S202). FIG. 8A shows an example of the teaching image.

When the teaching image is read, the image capturing function 52 roughly specifies positions of the lead part and the solder part (land part) with respect to each teaching image (at step S203). The image capturing function 52, as shown in FIG. 8B, has a template comprising a component body window 70, a lead window 71 and a land window 72. While enlarging or reducing the template and shifting the relative positions of the windows, the image capturing function 52 adjusts the windows 70, 71 and 72 to the component body, the lead and the land in the image, respectively. For the adjustment of the windows, for example, an image processing method such as template matching may be used. In addition, this adjustment (adjustment of the windows) may be roughly performed.

Subsequently, the pattern setting function 53 sets a plurality of patterns of color pickup regions for each teaching image (at step S204). This color pickup region comprises a first region for picking up a color of the lead part and a second region for picking up a color of the solder part. As shown in FIG. 8C, a first region 73 is disposed in the lead window 71 and a second region 74 is disposed in the land window 72. Respective configurations and sizes of the first and second regions 73 and 74 are defined by a relative value with respect to each window. According to this embodiment, three patterns of color pickup regions comprising a combination of one kind of first region and three kinds of second regions are used. A pattern A is a pattern for picking up a color from the entire boundary of the lead and the solder, a pattern B is a pattern for picking up a color from only the center of the boundary, and a pattern C is a pattern for picking up a color from only both ends of the boundary.

Then, the mapping function 54 maps the colors of all pixels in the first and second regions to a color histogram with respect to each of the patterns A to C (at step S205). At this time, the mapping is performed by using the pixels in the first region as a "target point" and the pixels in the second region as an "exclusion point" so that the target point and the exclusion point can be distinguished from each other. Here, the color histogram is provided by recording the frequency (the number) of pixels in each point in a color space. By the color histogram, color distributions of the pixels in the first and second regions can be grasped. In addition, the pixel denotes here the minimum resolution of an image. When the process of mapping a plurality of pixels is collectively executed, colors are mixed, so that it is preferable to perform the process from pixel to pixel.

Generally, the color space is a multidimensional space comprising the hue, chroma and lightness. Therefore, to accurately grasp the color distribution of the pixels, it is desirable to use the multidimensional color histogram in which the colors of pixels are mapped to the multidimensional color space.

Since red and blue are used as the light sources in the color highlight system, the blue color tends to appear in the solder part (second region) (this is because reflection close to specular reflection is generated on the solder surface). Furthermore, as described above the red color tends to appear in the lead part (first region). Therefore, if the purpose is to determine the color parameter to specify the boundary between the lead part and the solder part, it is sufficient to consider one color (blue or red, for example) or two colors (blue and red, for example). Thus, according to this embodiment, the blue color is selected as a hue which is included much in the second region and is hardly included in the first region and a two-dimensional color histogram in which pixel colors are mapped in a two-dimensional space comprising a chroma axis and a lightness axis of the blue color is used. Thus, an algorithm for finding an optimal solution of the color parameter can be extremely simplified. In addition, a two-dimensional color space comprising a chroma axis and a lightness axis of a red color (which is a hue included much in the first region and hardly included in the second region) may be used.

FIG. 8D shows an example of the two-dimensional color histogram. The horizontal axis in FIG. 8D indicates the chroma of blue, and the larger the plus value is, the higher a blue component is and the larger the minus value is, the higher a yellow component which is a complementary color of blue is. The vertical axis in FIG. 8D indicates the value of lightness, and the larger the value is, the higher the lightness is. A blank circle (○) in the histogram shows the target point and a painted triangle (▲) in the drawing shows the exclusion point. It can be seen that there is a difference in color distribution between the target point and the exclusion point and there is a difference in color distribution tendency in each pattern of the color pickup region.

Then, the pattern selecting function 55 calculates a degree in separation between a target point distribution and an exclusion point distribution in the color histogram for each of the patterns A to C (at step S206). According to this embodiment, as the degree in separation, a distance between the group of the target points and the group of the exclusion points is employed and it shall be arranged such that the larger the distance is, the larger the degree in separation is. In addition, various kinds of methods of calculating the distance between the groups have been proposed conventionally. Here, any method may be used. For example, the "Mahalanobis distance between the centroid of the exclusion point distribution and the target point distribution" and the "Euclidean distance between the centroids of the exclusion point distribution and the target point distribution" are considered. In addition, a method in which "a distance in the direction of the lightness axis is weighed to a distance between the centroids (to attach importance to the lightness)" using an experimental value may be used.

Then, the pattern selecting function 55 selects the pattern having the maximum degree in separation as the color pickup region used for determining the boundary (at step S207). According to the selected color pickup region here, since there is a conspicuous difference in color distribution between the first region (lead part) and the second region (solder part), the boundary between the lead and the solder can be determined with high precision.

Figure 9A:
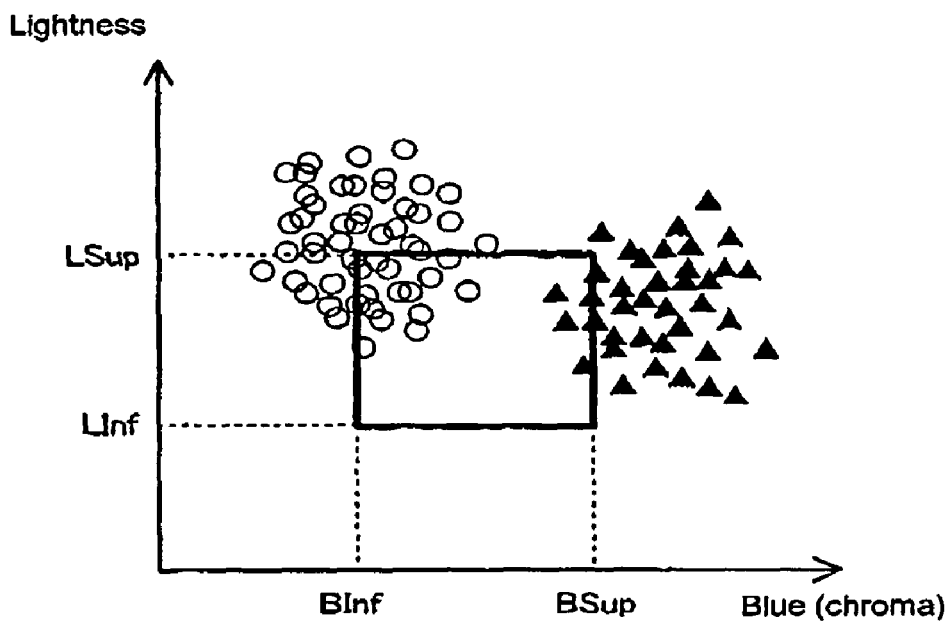
FIG. 9 shows a searching process of a color range.

Next, the color range searching function 56 searches for a color range which optimally separates the color distribution of the target points and the color distribution of the exclusion points from each other in the selected pattern on the basis of the two-dimensional color histogram (at step S208). According to this embodiment, as shown in FIG. 9A, to simplify its algorithm, a rectangular color range comprising four values of a lower limit (BInf) and an upper limit (BSup) of chroma and a lower limit (LInf) and an upper limit (LSup) of lightness is provided. The optimum solution to be obtained here is a color range which includes the target points (○) as many as possible and hardly includes the exclusion points (▲).

Figure 9B:
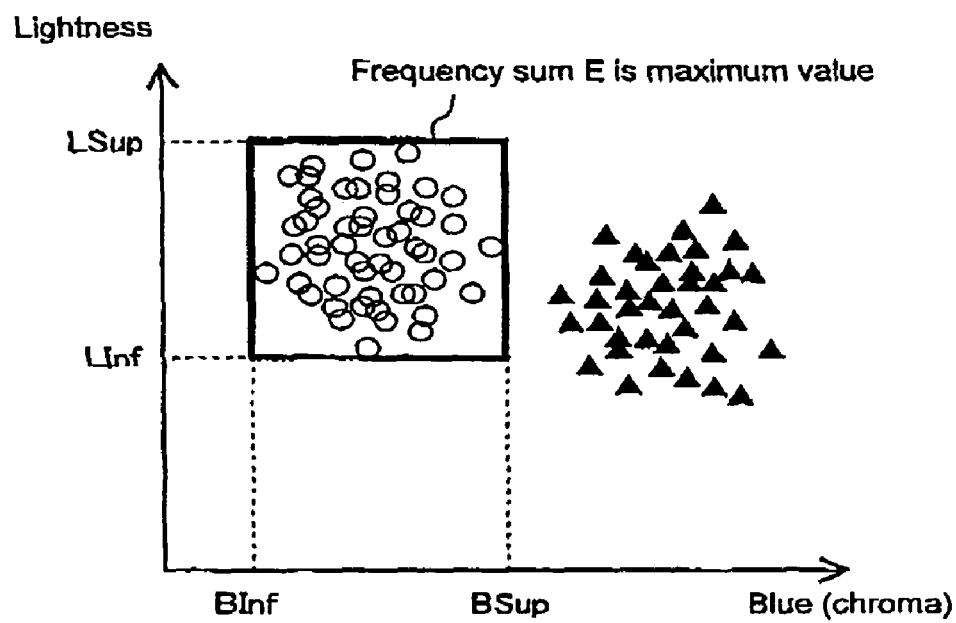

Concretely, the color range searching function 56 calculates a frequency sum E of the color range while changing each of the values BInf, BSup, LInf and LSup (see Equation 1) and obtains a color range in which the frequency sum E is a maximum value. The frequency sum E indicates an index showing a difference between the number (frequency) of the target points and the number (frequency) of the exclusion points included in the color range. FIG. 9B shows the color range in which the frequency sum E is the maximum value.

$$E = \sum_{b=BInf}^{BSup} \sum_{l=LInf}^{LSup} \{S(b, l) - R(b, l)\}$$ [Equation 1]

$b$: chroma $l$: lightness $S(b, l)$: frequency of target point at point $(b, l)$ $R(b, l)$: frequency of exclusion point at point $(b, l)$.

The color range searching function 56 sets the color range in which the frequency sum E is the maximum value as the first color parameter (color condition) for the inspection target region determining process (at step S209). Thus, according to this embodiment, the color parameter to distinguish the color of the lead part (target point) from the color of the solder part (exclusion point) properly can be automatically generated.

Then, the process for automatically generating the first determination condition (defined width and defined width line number) for the inspection target region determining process is executed using the above color parameter.

Figure 10A:
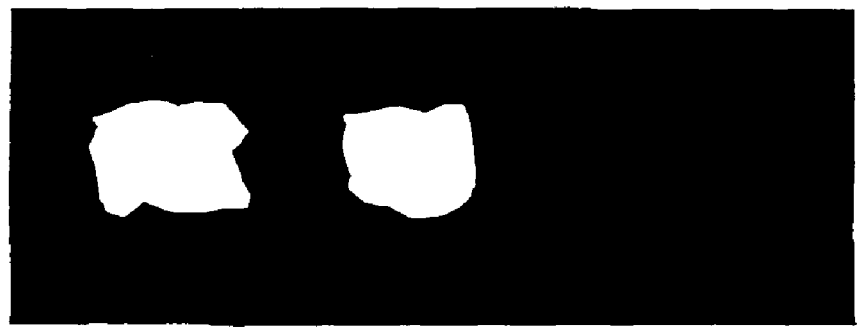
FIG. 10 shows a calculating process of a first determination condition.

First, the binarizing function 57 converts the teaching image into an image in the binary form by using the first color parameter (at step S210). In this binarizing process, the pixels included in the color range defined by the color parameter are converted to the white pixels and the pixels other than the above pixels are converted to the block pixels. FIG. 10A shows a binarized result of the teaching image. FIG. 10A shows a result of the binarizing process of the teaching image. As shown in FIG. 10A, a large white pixel region appears in the lead part. When this binarized image is used, it is easy to calculate the feature for identifying the boundary between the lead and the solder quantitatively.

The determination condition calculating function 58 statistically analyzes the feature of the white pixel region of each teaching image to automatically calculate the condition (defined width and defined width line number) for determining the boundary between the lead part and the solder part as will be described below.

First, a candidate boundary range is determined by using the specified result (template matching result) of the lead part and the solder part provided at the step S203 (at step S211). More specifically, a range of ±α pixels across the boundary between the lead window 71 and the land window 72 is determined as the candidate boundary range (α may be any number although α=2 in this example). That is, on the basis of a fact that "a true boundary exists close to the boundary of the template matching result", the boundary searching process is simplified by narrowing the boundary existing range.

Then, the determination condition calculating function 58 sets a search range of the width and the line number as follows (at step S212). In addition, the width is defined at a ratio with respect to the width of the lead window 71.

Width: Wmin to Wmax (%) (Wmin and Wmax may be any number although Wmin=40% and Wmax=90% in this example)

Line number: Lmin to Lmax (Lmin and Lmax may be any number although Lmin=1 and Lmax=5 in this example)

Figure 10B:
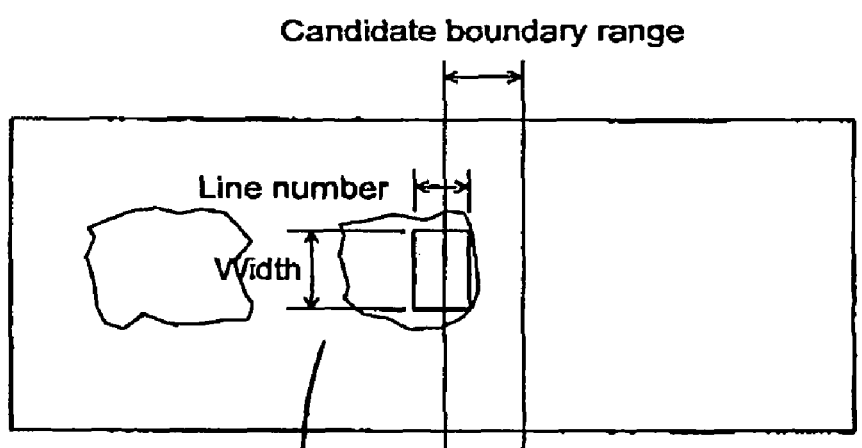
Figure 10C:
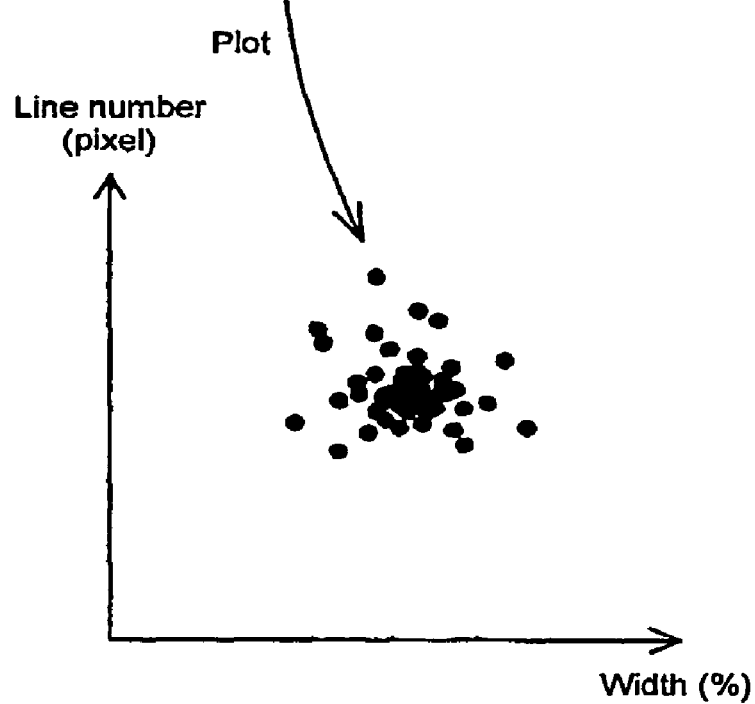
Figure 11:
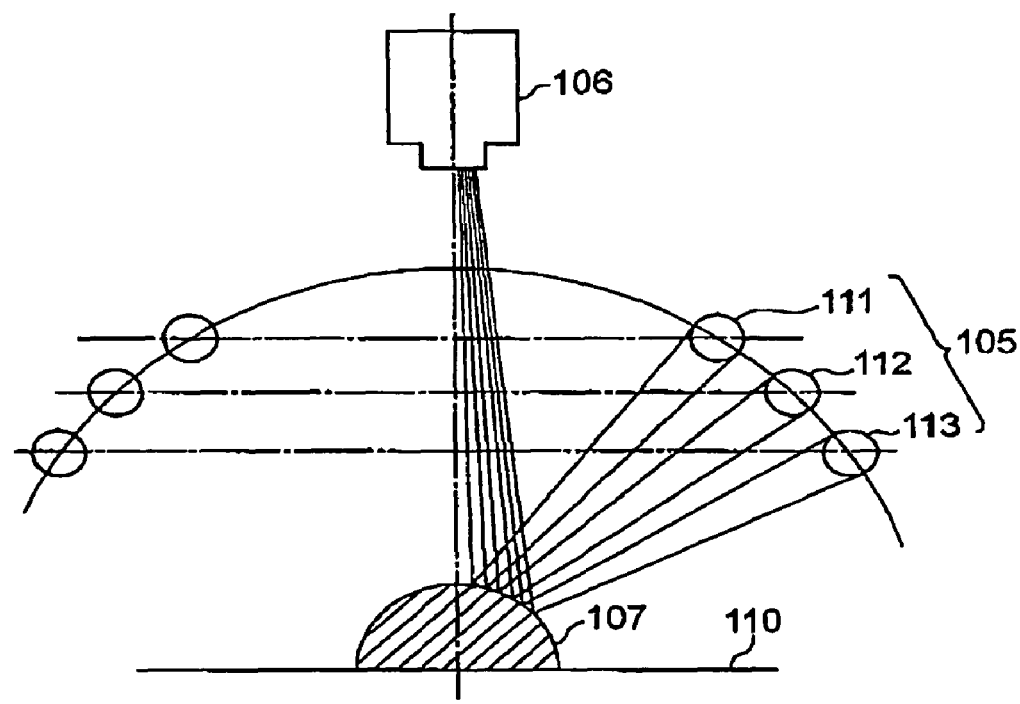
FIG. 11 shows a constitution of a board inspecting apparatus of a color highlight system.
Figure 12:
FIG. 12 shows an example of a color pattern appearing in a captured image.
Figure 13:
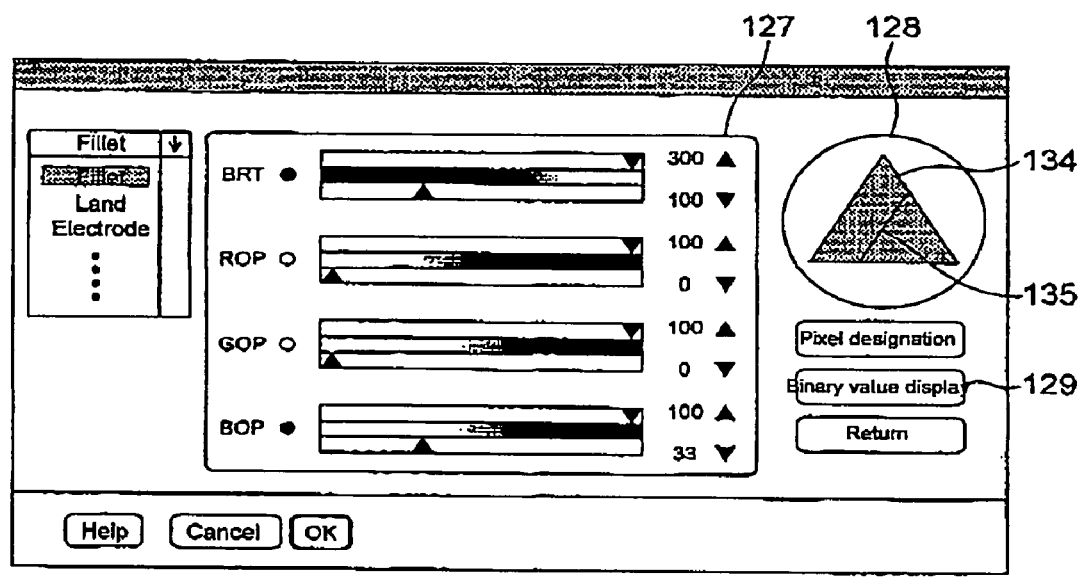
FIG. 13 shows a setting support tool of a color parameter.
Figure 14A:
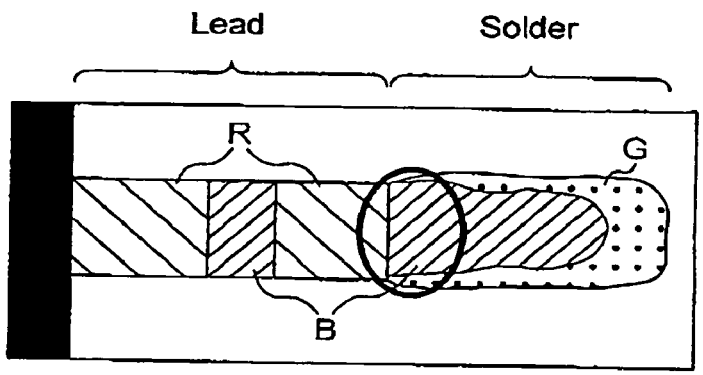
FIG. 14 shows a difference in color distribution tendency at a solder part due to a difference in component kind.
Figure 14B:
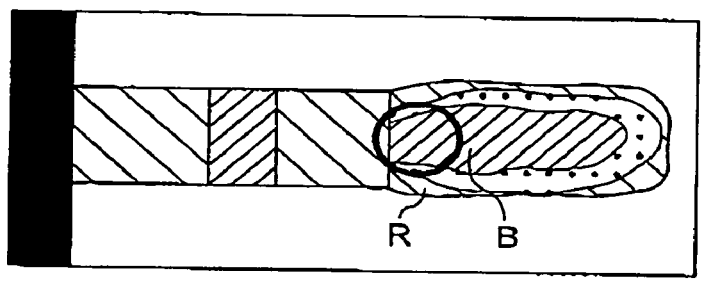
Figure 14C:
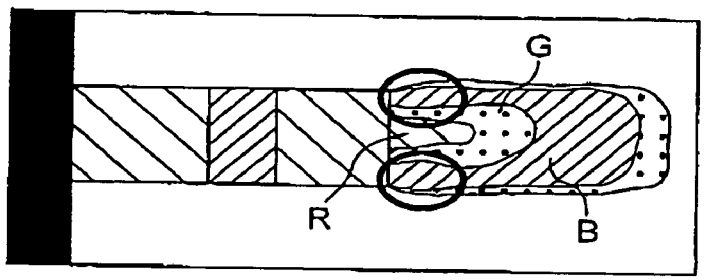

Next, the determination condition calculating function 58 searches for rectangles that satisfy a condition such that the rectangles are included in the white pixel region and their widths and line numbers (lengths) are included in the above search range and their ends (edges) are included in the above candidate boundary range (at step S213) (see FIG. 10B). Thus, the rectangle having the largest area value is selected from the searched rectangles and the width and the line number of the selected rectangle are plotted on a graph (at step S214) (see FIG. 10C).

When the plotting for the all teaching images is completed, the determination condition calculating function 58 sets the width and line number that are most frequently plotted to the defined width and the defined width line number which are the first determination condition for the inspection target region determining process (at step S215).

Thus, the parameters necessary for the inspection target region determining process are automatically generated.

Then, the inspection logic generating function 59 generates the first parameter set of the inspection logics from the first color parameter, the defined width and the defined width line number (at step S216) and the inspection logic writing function 60 writes the first parameter set to the inspection logic storage 35 of the board inspecting apparatus 1 (at step S217). Thus, the parameter setting process for the inspection target region determining process is completed.

In addition, according to the second parameter set for the inspecting process, it is automatically generated by parameter setting apparatus 2 or it is manually generated. When it is automatically generated, an inspection target region (solder part) is extracted from the good and defective teaching images using the first parameter set, and pixels included in the inspection target region of the good image and pixels included in the inspection target region of the defective image are mapped as the target point and the exclusion point, respectively to the two-dimensional color histogram, and the second color parameter for distinguishing the target point from the exclusion point is generated like the above. In addition, regarding the second determination condition, each of the good image and the defective image is binarized by the second color parameter to calculate a threshold value for determining the quality on the basis of the difference in feature (area value and the like) in the white pixel region. The generated second parameter set is also stored in the inspection logic storage 35.

According to the embodiment described above, since the color pickup region having the largest difference in color distribution between the lead part and the solder part is selected, the parameters for specifying the boundary between the lead part and the solder part can be automatically generated even from the teaching image having a variation in color distribution tendency, so that the teaching operation can be simplified and the teaching can be automatically performed. As a result, the inspection target region (solder part) can be extracted with high precision by using the parameters, so that the precision and reliability of the board inspection can be improved.

The above embodiment is only illustrated as one example of the present invention. Various kinds of modifications and variations may be added to the illustrated embodiments within the same or equal scope of the present invention.

Furthermore, although the two-dimensional color histogram (color space) is used in the above embodiment, multi-dimensional (hue, chroma and lightness) color histogram may be used. In addition, regarding the two-dimensional color histogram, a chroma axis of another hue such as blue, green or yellow is used instead of the red chroma axis, or a hue axis may be used instead of the chroma axis. Selection of the axis of the color histogram may be determined according to the tendency of the color pattern of the component image taken by the board inspecting apparatus.

In addition, the color range is not limited to the rectangle, so that a circle, a polygon or a free curved line may be used. Furthermore, when the color histogram is the multidimensional one, the color range has preferably a multidimensional configuration also.

What is claimed is:

1. A parameter setting method of automatically generating a parameter used in a board inspecting process in a board inspecting apparatus which irradiates a mounted component on a board with a plurality of color rays at different incident angles and in order to define a boundary between a first part and a second part adjacent to the first part on the board in an image captured from their reflected lights, extracts a region that satisfies a predetermined color condition for defining a color having a tendency to appear in the first part, from the image and determines the boundary by comparing a feature of the extracted region with a predetermined determination condition, with steps comprising:

capturing a plurality of teaching images by taking images of components;

setting a plurality of patterns of color pickup regions each comprising a first region for picking up a color of the first part and a second region for picking up a color of the second part for each of the teaching images;

mapping a color of each pixel in the first region and a color of each pixel in the second region as a target point and an exclusion point, respectively, to a multidimensional color space comprising chroma and lightness for each of the patterns of the color pickup regions;

calculating a degree in separation between a target point distribution and an exclusion point distribution in the color space for each of the patterns of the color pickup regions;

selecting a pattern of a color pickup region in which the degree in separation has a maximum value;

finding a color range which divides the color space and has the largest difference between the number of target points and the number of exclusion points in the selected pattern; and setting the found color range as a color condition used for the board inspecting process.

2. The parameter setting method of the board inspecting apparatus according to claim 1, wherein the color space is a two-dimensional color space comprising a chroma axis and a lightness axis regarding a hue having a tendency to be included much in the first part and hardly included in the second part or a hue having a tendency to be included much in the second part and hardly included in the first part.

3. The parameter setting method of the board inspecting apparatus according to claim 2, wherein the color condition comprises lower and upper limit values of chroma and lower and upper limit values of lightness.

4. The parameter setting method of the board inspecting apparatus according to claims 1, with steps further comprising:

extracting a pixel region that satisfies the color condition from each teaching image;

calculating a condition for determining a boundary between the first and second parts by statistically analyzing a feature of the pixel region; and setting the calculated condition as a determination condition used for the board inspecting process.

5. A parameter setting apparatus for automatically generating a parameter used in a board inspecting process in a board inspecting apparatus which irradiates a mounted component on a board with a plurality of color rays at different incident angles and in order to define a boundary between a first part and a second part adjacent to the first part on the board in an image captured from their reflected lights, extracts a region that satisfies a predetermined color condition for defining a color having a tendency to appear in the first part, from the image and determines the boundary by comparing a feature of the extracted region with a predetermined determination condition, comprising:

an image capturing device for capturing a plurality of teaching images by taking images of components;

a pattern setting device for setting a plurality of patterns of color pickup regions each comprising a first region for picking up a color of the first part and a second region for picking up a color of the second part for each of the teaching images;

a mapping device for mapping a color of each pixel in the first region and a color of each pixel in the second region as a target point and an exclusion point, respectively, to a multidimensional color space comprising chroma and lightness for each of the patterns of the color pickup regions;

a pattern selecting device for calculating a degree in separation between a target point distribution and an exclusion point distribution in the color space for each of the patterns of the color pickup regions and selecting a pattern of a color pickup region in which the degree in separation has a maximum value;

a color range searching device for finding a color range which divides the color space and has the largest difference between the number of target points and the number of exclusion points in the selected pattern; and a color condition setting device for setting the found color range as a color condition used for the board inspecting process.

6. The parameter setting apparatus of the board inspecting apparatus according to claim 5, wherein the color space is a two-dimensional color space comprising at least a chroma axis and a lightness axis regarding a hue having a tendency to be included much in the first part and hardly included in the second part or a hue having a tendency to be included much in the second part and hardly included in the first part.

7. The parameter setting apparatus of the board inspecting apparatus according to claim 6, wherein the color condition comprises lower and upper limit values of chroma and lower and upper limit values of lightness.

8. The parameter setting apparatus of the board inspecting apparatus according to claim 5, further comprising a region extracting device for extracting a pixel region that satisfies the color condition from each teaching image;

a condition determining device for calculating a condition for determining a boundary between the first and second parts by statistically analyzing a feature of the pixel region; and a determination condition setting device for setting the calculated condition as a determination condition used for the board inspecting process.

9. A board inspecting apparatus comprising:

storage for storing the color condition and the determination condition set by the parameter setting apparatus according to claim 8;

a light emitter for irradiating a mounted component on a board with a plurality of color rays at different incident angles;

a boundary determining device for determining a boundary between a first part and a second part adjacent to the first part on the board in an image of their reflected light by extracting a region that satisfies the color condition from the image and comparing a feature in the extracted region with the determination condition to specify the boundary; and an inspecting device for extracting an inspection target region on the basis of the boundary and inspecting the inspection target region.

* * * * *